United States Patent [19]

Monthony et al.

[11] Patent Number: 5,313,959
[45] Date of Patent: May 24, 1994

[54] DEVICE AND METHOD FOR BREAKING AN AMPOULE

[75] Inventors: James F. Monthony, Baltimore; Dwight Livingston, Towson, both of Md.

[73] Assignee: Becton, Dickinson and Company, Franklin Lakes, N.J.

[21] Appl. No.: 50,521

[22] Filed: Apr. 21, 1993

[51] Int. Cl.$^5$ ............................................. A61B 10/00
[52] U.S. Cl. .................................... 128/759; 206/361
[58] Field of Search ................... 128/749, 757, 759; 206/361, 438; 435/30, 287

[56] References Cited

U.S. PATENT DOCUMENTS

| | | | |
|---|---|---|---|
| 3,450,129 | 6/1969 | Avery et al. | 128/2 |
| 3,891,331 | 6/1975 | Avery | 401/132 |
| 3,924,623 | 12/1975 | Avery | 128/269 |
| 4,014,748 | 3/1977 | Spinner et al. | 195/127 |
| 4,023,934 | 5/1977 | Spinner et al. | 23/254 |
| 4,196,167 | 4/1980 | Olsen | 128/759 |
| 4,211,323 | 7/1980 | Olsen | 206/210 |
| 4,311,792 | 1/1982 | Avery | 435/30 |
| 4,353,868 | 10/1982 | Joslin et al. | 422/101 |
| 4,586,604 | 5/1986 | Alter | 206/210 |
| 4,604,360 | 8/1986 | Hounsell | 435/287 |
| 5,096,062 | 3/1992 | Burkardt et al. | 206/361 |
| 5,238,649 | 8/1993 | Nason | 128/759 |

FOREIGN PATENT DOCUMENTS 0420450  9/1989  European Pat. Off. ...... C12M 1/30

Primary Examiner—Max Hindenburg
Attorney, Agent, or Firm—Nanette S. Thomas

[57] ABSTRACT

The present invention is a device and method for breaking an ampoule. In particular, the device is preferably for use in an apparatus for collecting and transporting biological specimens. The device comprises a guard arrangement that surrounds a frangible ampoule. With appropriate force applied to the guard arrangement, the frangible ampoule is ruptured.

16 Claims, 5 Drawing Sheets

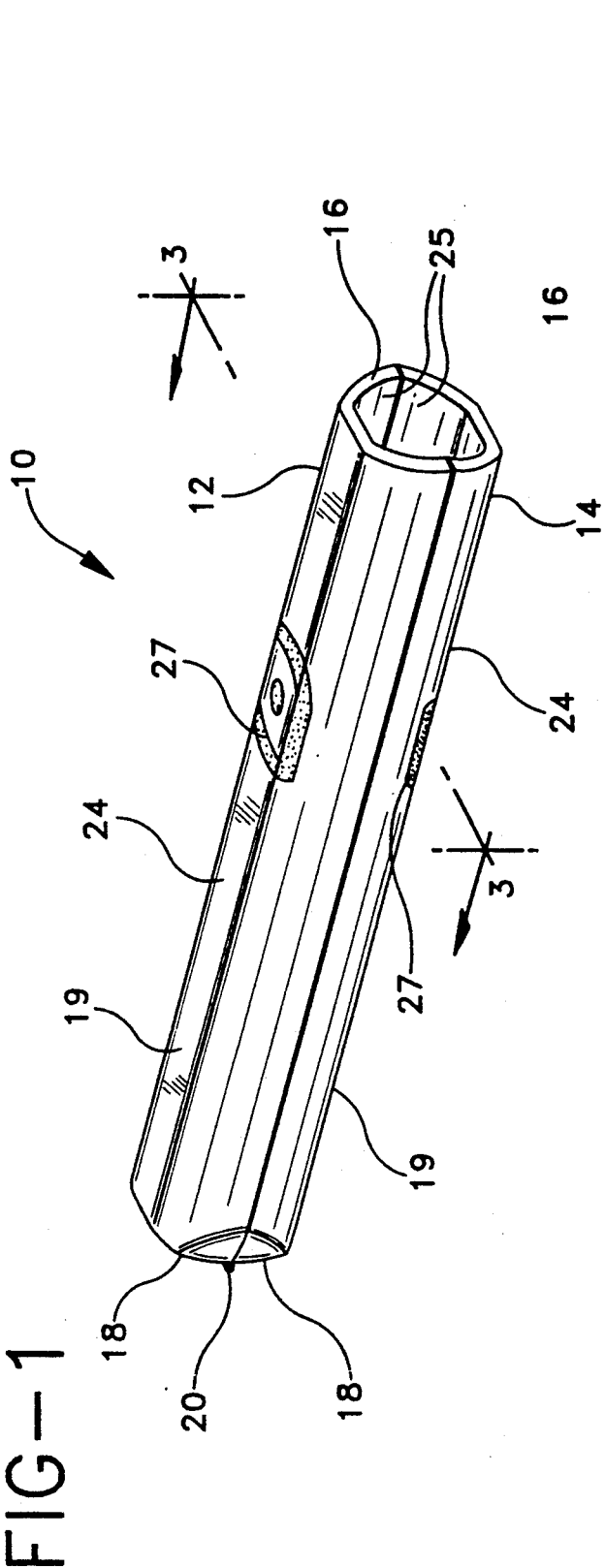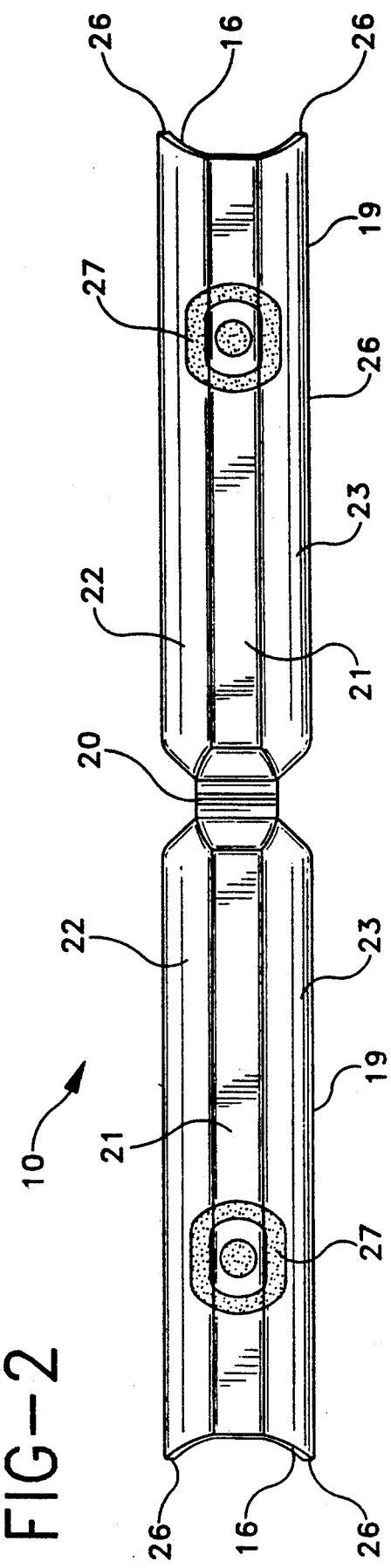

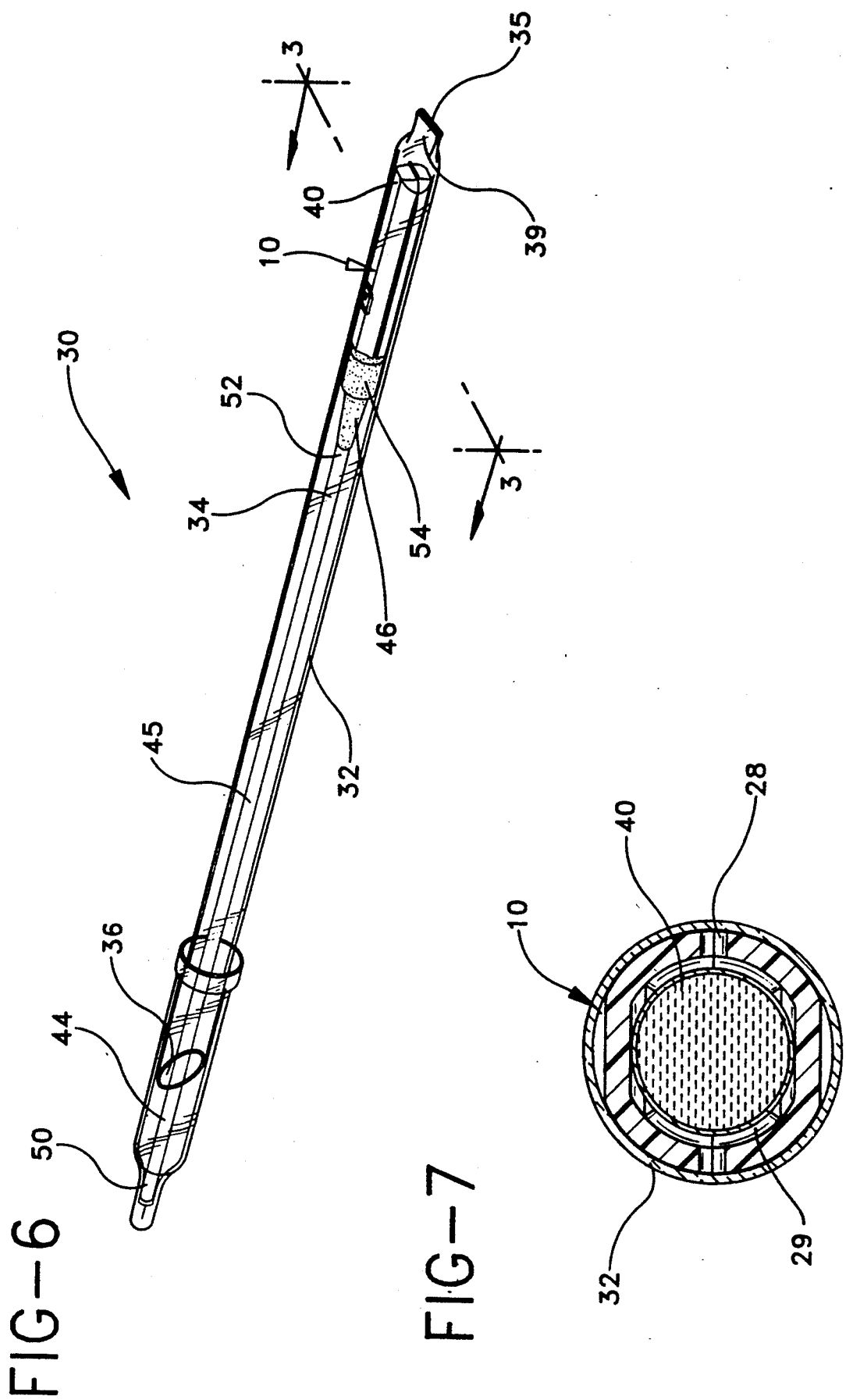

DEVICE AND METHOD FOR BREAKING AN AMPOULE

BACKGROUND OF THE INVENTION

1. Field of the Invention

This invention relates to a device and method for breaking ampoules. In particular the device may be used for breaking ampoules in an apparatus for collecting and transporting biological specimens.

2. Description of Related Art

An element common to most devices for collecting and transporting biological specimens is an ampoule in a container that can be broken to release medium into the container to keep the swab and sample moist. A typical collecting and transporting device has been described in several publications and most specifically in U.S. Pat. No. 4,014,748.

A commercially available device for collecting and transporting biological specimens is the CULTURETTE ® Collection and Transport System (trademark of Becton, Dickinson and Company) sold by Becton Dickinson Microbiology Systems, Cockeysville, Md. The CULTURETTE device is for collecting and transporting a biological sample with a protective sleeve or skirt surrounding the container where the ampoule, which is to be broken for use, is contained.

A problem that has confronted users of collection and transport devices is maintaining the viability and preventing the contamination of any biological sample which is collected. In spite of the use of a high level of skill and care in collecting the specimen so as to prevent contamination of the specimen, viability of the microorganisms is not always assured by the use of the prior art collection devices.

With the increased emphasis on the efficacy of medical products, a need exists for an improved device and method for effectively and efficiently handling ampoules. Such a device would be comparatively simple and inexpensive to manufacture as compared to available devices.

SUMMARY OF THE INVENTION

The present invention is a device and method for breaking ampoules. In particular, the device may be used in an apparatus for collecting and transporting biological specimens to substantially prevent the specimen collected in the apparatus from being exposed to the outside environment.

The device is preferably a guard arrangement having two rigid, movable and opposing members spaced sufficiently from one another surrounding an ampoule. The movable members extend from a forward end to a rearward end. Desirably the movable members are folded together at the rearward end. Preferably the movable members are connected by a living hinge at the rearward end.

Preferably each member comprises a wall with an outer surface, an inner surface and an edge. The inner surfaces face each other to form a cavity that surrounds an ampoule and the edges face each other to form a gap. The ampoule may be placed or attached in the cavity between the inner surfaces of the members while maintaining a gap between the edges. Preferably the diameter of the cavity is greater than the diameter of the ampoule.

As the members are compressed, the edges of the members are brought together so there is no gap, the diameter of the cavity of the guard arrangement is reduced and the ampoule is ruptured. The compressed or reduced cavity in turn effects a force on the ampoule so that the ampoule will deform and rupture.

Most preferably the wall thickness of each member is greater than the gap that is formed between the edges of the members when the guard arrangement surrounds an ampoule. The wall thickness substantially reduces or limits fragments of a ruptured ampoule from penetrating the walls of each member.

Desirably each member has a curved wall in the shape of an arch, oval or the like. Most preferably the wall of each member has three sides. The sides are desirably in the shape of an arch, oval or the like. Most preferably the walls of the members are the same or symmetrical in shape.

The guard arrangement and ampoule may be preferably included in an apparatus for collecting and transporting biological specimens. Preferably the apparatus comprises a tubular housing, a specimen collector, a guard arrangement and a frangible ampoule located within the tubular housing. Desirably, the frangible ampoule holds medium that may be released into the tubular housing.

To collect and transport a specimen, the specimen collector is removed from the tubular housing. A site, such as the area of the throat, nose, ears, mouth, wound or operative sites, is sampled by contacting the site with the swab of the specimen collector. The specimen is removed from the site with the swab. Thereafter the specimen collector is preferably returned to the tubular housing with the swab being preferably positioned in contact with a swatch or pledget. The user then effects a force, such as finger pressure, on the tubular housing where the guard arrangement and ampoule are located. This in turn compresses the guard arrangement so that the edges of the members are brought together so there is no gap, the cavity is reduced so there is not sufficient area for the ampoule and as a result the ampoule is ruptured. The ruptured ampoule releases medium into the housing wherein fragments of the ruptured ampoule are substantially limited from penetrating the walls of each member.

The guard arrangement of the present invention improves the standard collection type device in that microorganisms that are obtained by the collection device may remain substantially viable and uncontaminated through the entire specimen collection, transport, storage and identification phases.

DESCRIPTION OF THE DRAWINGS

FIG. 1 is a perspective view of the preferred guard arrangement embodiment of the present invention, illustrated in its folded condition.

FIG. 2 is a top view of the guard arrangement of FIG. 1 in its unfolded condition.

FIG. 6 is a perspective view illustrating a device for collecting and transporting specimens with the guard arrangement of FIG. 1.

FIG. 7 is a cross-sectional view of FIG. 6 taken along lines 7—7.

DETAILED DESCRIPTION

Figure 5:
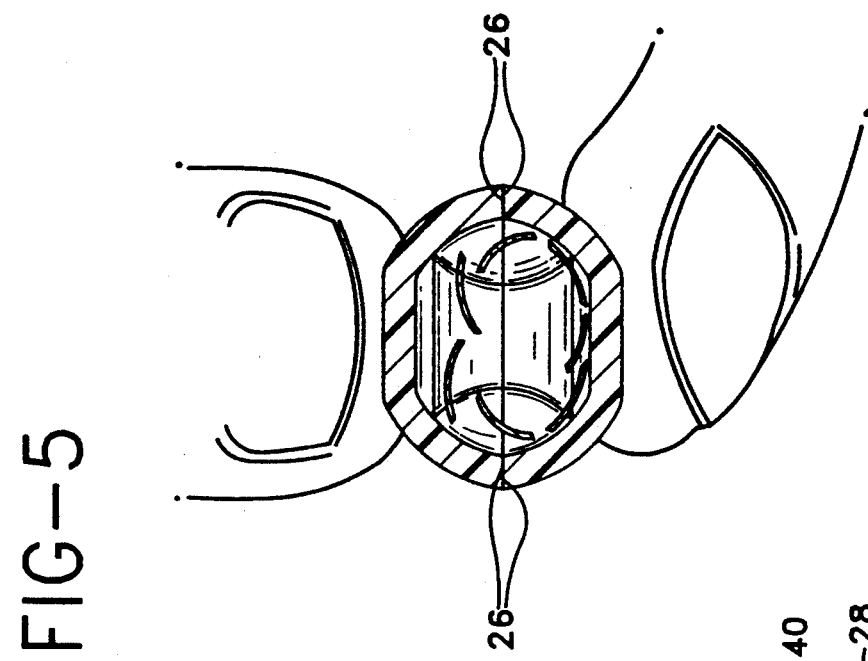
FIG. 5 is a cross sectional view of FIG. 4 taken along lines 5—5 illustrating the breaking of an ampoule.

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

The preferred guard arrangement 10 of the present invention in its folded condition as illustrated in FIG. 1, comprises two rigid, movable and opposing members 12 and 14 that extend from a forward end 16 to a rearward end 18 and are connected by a living hinge 20 at the rearward end. Each member comprises a sidewall 19 with an outer surface 24 and inner surface 25 and preferably the outer surface of each member is marked with indicia 27.

Figure 3:
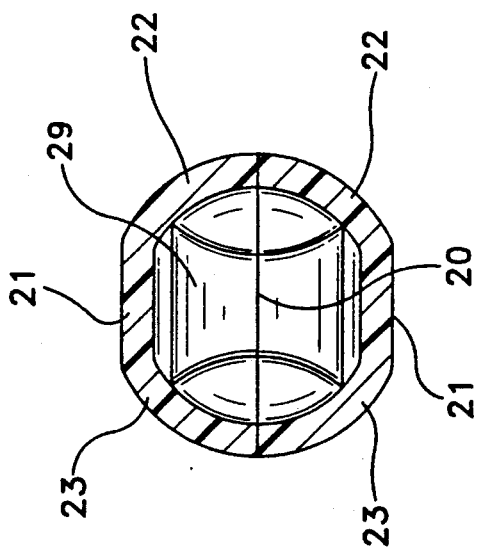
FIG. 3 is a cross sectional view of FIG. 1 taken along line 3—3 thereof.

In its unfolded arrangement, as shown in FIG. 2, each sidewall preferably has three sides 21, 22 and 23, with sides 22 and 23 extending from side 21. As shown in FIG. 3, sides 22 and 23 extend from side 21 at an angle preferably less than 0.45 degrees to an edge 26. In its folded arrangement, the inner surfaces of the opposing members face the other to form a cavity 29 and the edges of the opposing members also face each other. The distance from side 23 to side 22 of each member is greater than the height of cavity 29 or the distance between sides 21 of the members.

Figure 4:
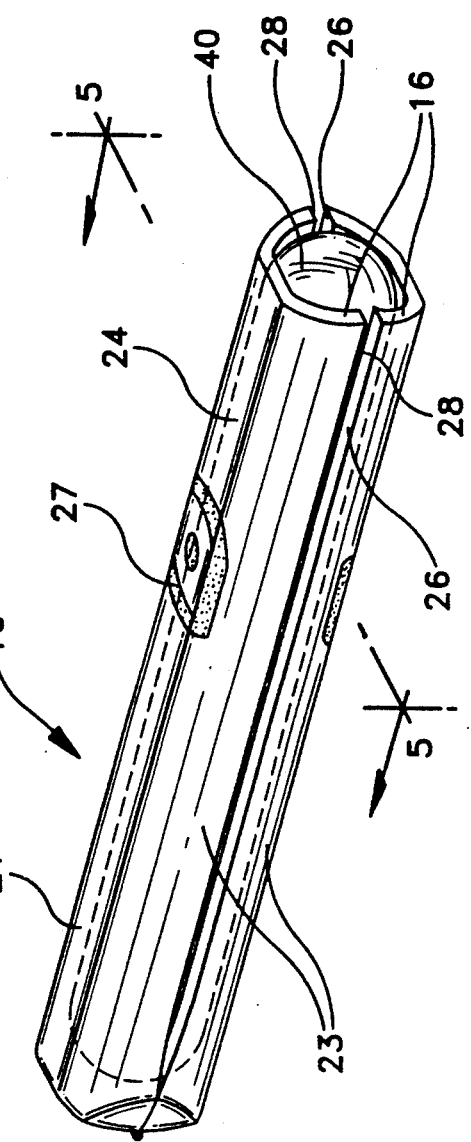
FIG. 4 is a perspective view of the preferred guard arrangement of the present invention, including an ampoule.

In a preferred embodiment of the invention, as shown in FIG. 4, the guard arrangement substantially surrounds a sealed frangible ampoule 40 with a space 28 between the edges of the members. The ampoule may if desired, be secured to the inner surfaces of the guard arrangement with an adhesive.

As shown in FIG. 5, the frangible ampoule is ruptured when the user applies finger pressure at the marked indicia on the guard arrangement so that the edges of the members are brought together and the cavity is compressed or reduced so there is not sufficient area for the frangible ampoule. As a result, the compressed cavity in turn effects a force on the ampoule to cause it to rupture.

The guard arrangement and frangible ampoule may be used in a collection device 30 as illustrated in FIG. 6. Device 30 preferably comprises a tubular housing 32 and a specimen collector 34. Tubular housing 32 has a closed end extremity 35 and an opposite open end extremity 36. The tubular housing is sealed at closed end extremity 35, leaving surface 39 to which may be affixed by heat stamp, imprinting or other means a lot number or identification to enable traceability throughout the life of device 30.

Device 30 also includes a cap 44, a shaft 45, and a swab 46. Cap 44 is preferably removably attachable to the open end extremity of the tubular housing. The cap is preferably adapted to telescope snugly, but slidably, over the open end extremity of the tubular housing before and after swab 46 is used.

Shaft 45 comprises a first end 50 and a second end 52. First end 50 is preferably connected to the cap and second end 52 is preferably connected to swab 46. The swab is contained within the tubular housing. Swab 46 is preferably made from soft and absorbent materials including but not limited to suitable fibrous materials such as cotton, polyester fibers or the like.

Disposed within the tubular housing and adjacent the closed end extremity is frangible ampoule 40. The frangible ampoule preferably holds liquid medium which may be released inside the tubular housing. The liquid in the ampoule may be a transport medium which provides an environment in which the specimen can remain substantially viable. Frangible ampoule 40 is preferably made of, but not limited to, glass or some other frangible or rupturable material which is substantially non-reactive with the liquid therein.

Substantially surrounding the frangible ampoule is guard arrangement 10. The guard arrangement is preferably oriented so that the rearward end is at the closed end extremity of the tubular housing. To retain the loose frangible ampoule and the surrounding guard arrangement in this position and also to restrain flow of released liquid, an absorbent plug 54 is located within the tubular housing. The absorbent plug may be tightly telescoped within the tubular housing and preferably abuts the frangible ampoule and the surrounding guard arrangement to prevent the latter from sliding. Absorbent plug 54 may be made of cotton-like material or any other suitable material having absorbing properties, for properly restraining flow and/or fragments or particulate matter.

The swab is also preferably in contact with the absorbent plug and thus, as liquid is released from the frangible ampoule, the absorbent plug is moistened and in turn conducts the moisture to the swab. The liquid provides a moist environment for the specimen on the swab, to keep the specimen substantially viable during transport and to prevent dehydration of the specimen. In addition, the absorbent plug may substantially prevent fragments of the frangible ampoule from collecting on the swab after the frangible ampoule has been broken.

In some cases, the absorbent plug may not be employed in the tubular housing, however, it is a preferred element, especially when the liquid in the ampoule has a low viscosity. When the liquid has a low viscosity, the metering effect of the absorbent plug prevents the liquid and portions of the specimen from spreading onto the shaft or onto the interior face of the cap and thus prevents contamination of these parts.

Figure 8:
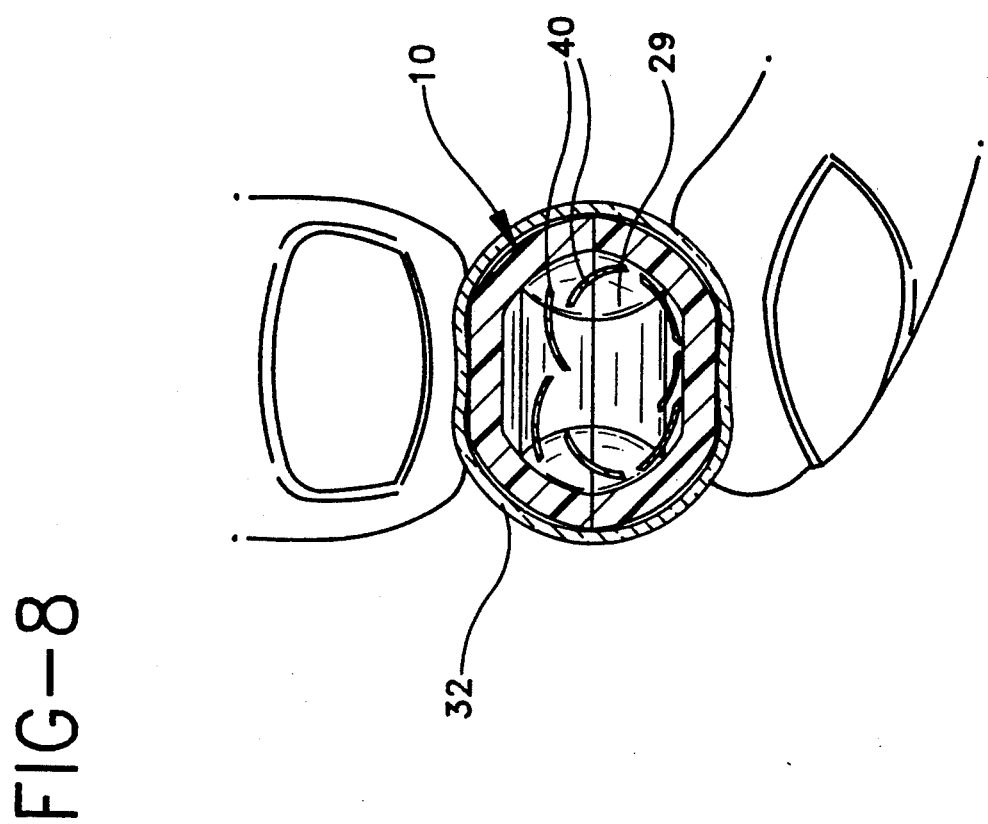
FIG. 8 is the cross sectional view of FIG. 7 illustrating the breaking of the ampoule.

As shown in FIG. 7, the frangible ampoule is located within cavity 29 of the guard arrangement. The guard arrangement substantially surrounds the ampoule while having a space between the edges of the members. As shown in FIG. 8, as the edges of the members are brought together and the cavity is compressed or reduced, the frangible ampoule is ruptured. The user applies finger pressure to the outer surface of the tubular housing section at the locations marked on the guard arrangement. The force on the tubular housing in turn effects a force on the guard arrangement so that the edges of the members are brought together and the cavity is compressed or reduced and there is not sufficient area for the ampoule. The compressed or reduced cavity in turn effects a force on the ampoule so that the ampoule breaks and liquid is released therein. A frangible ampoule made of glass is most preferred because it can be easily and effectively sterilized by autoclaving and it does not react either with the medium and/or the specimen collected.

The liquid in the ampoule may be various well known liquid media. The particular medium used is chosen on the basis of the particular type of culture to be preserved in the specimen collected. A liquid medium such as Stuart's Modified Media or a liquid culture of bile, blood or egg may be used. Gel-type media may also be used.

The tubular housing is most preferably an optically clear plastic and the guard arrangement an opaque plastic. The opaque plastic highlights where the frangible ampoule is located or the type of medium enclosed in the ampoule.

Preferably, the tubular housing is made of easily compressible material so that guard arrangement, if employed in the device, may rupture the ampoule simply by applying pressure to the tubular housing.

To collect a specimen, cap 44 is removed from tubular housing 32 and swab 46 is pulled out of the tubular housing. A particular body passage of the patient then is swabbed with swab 46 to obtain a specimen. Thereafter, the swab with the specimen is returned to the tubular member with the swab being positioned in contact with absorbent plug 54. The user then effects a force on the tubular housing at the locations marked with indicia on the guard arrangement to bring the edges of the members together. In turn the cavity is compressed or reduced so there is not sufficient area for the ampoule. The compressed or reduced cavity in turn effects a force on the ampoule so that the ampoule breaks and liquid is released. The liquid moistens the absorbent plug which, in turn, moistens the swab to keep the specimen in suitable condition until it reaches, for example, a laboratory or related facility for testing.

Figure 9:
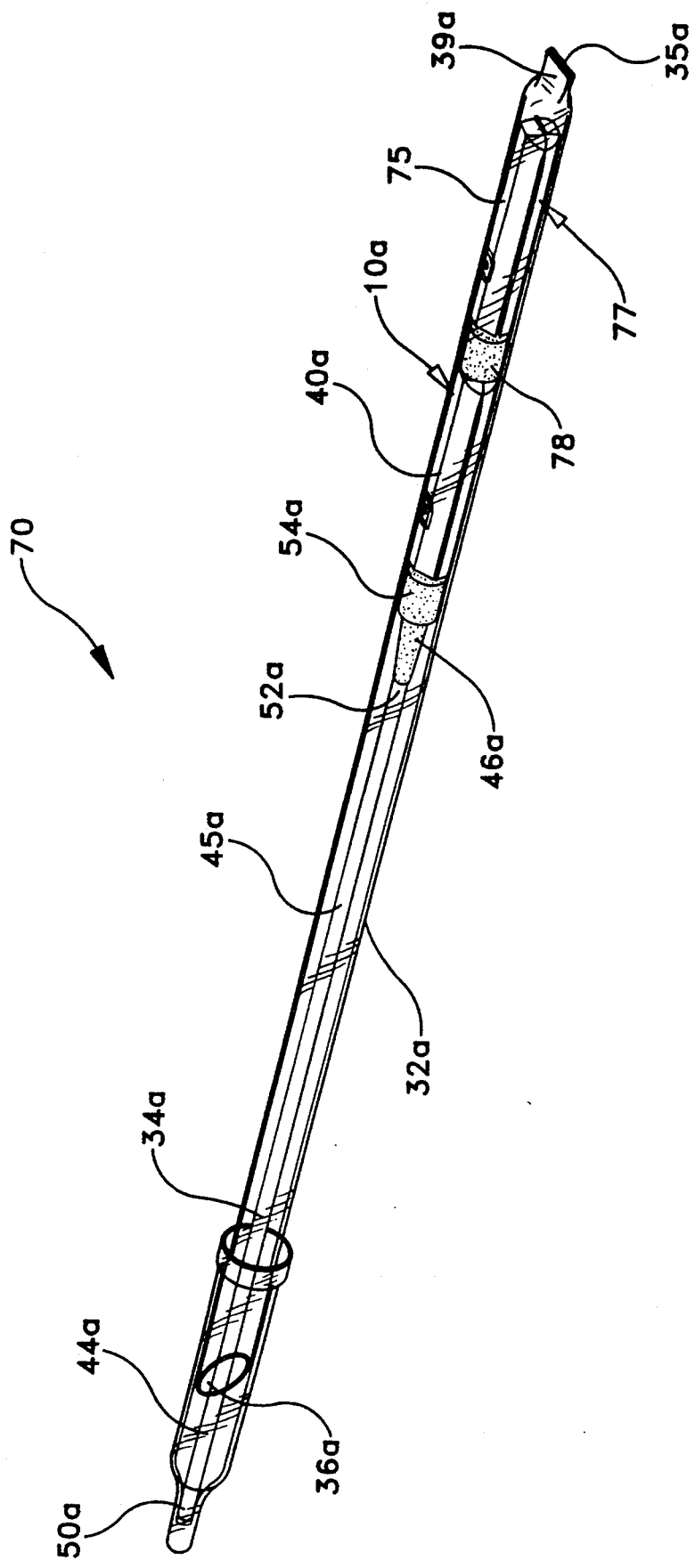
FIG. 9 is a perspective view illustrating a system for collecting and transporting specimens comprising at least two ampoules with respective guard arrangements.

An alternate embodiment of a collection device is shown in, FIG. 9, that includes many components of FIGS. 6–8. Accordingly, similar components performing similar functions will be numbered identically to those components of FIGS. 6–8, except that a suffix "a" is used to identify those similar components in FIG. 9.

FIG. 9 illustrates a collection device 70 that has disposed within tubular housing 32a, adjacent absorbent plug 54a, a second frangible ampoule 75 within a second guard arrangement 77. Second frangible ampoule 75 is preferably made, but not limited to the same materials as frangible ampoule 40a. Second frangible ampoule 75 preferably holds a test reagent which may be released inside the tubular housing. The test reagent may be used to detect and identify microorganisms and for receiving detectable antigen in the device. To retain the second frangible ampoule and second guard arrangement in position and also to restrain flow of released test reagent, a second absorbent plug 78 is located within the tubular housing. The absorbent plug is tightly telescoped within the tubular housing and abuts the second frangible ampoule and guard arrangement to prevent the latter from sliding.

The test reagent that is preferably held in the second frangible ampoule may be one or more of various well known test reagents. The particular test reagent used may be chosen on the basis of the particular type of species being identified. A test reagent such as N,N,N,N-tetra-methyl-p-phenylenediamine dihydrochloride may be used as disclosed in U.S. Pat. No. 3,876,503, which is hereby incorporated by reference, for detecting gonorrhea. Other test reagents such as di-methyl-amino-cinnaminaldehyde, beta-d-galactosidase substrates, gamma-glutamylamino peptidase and prolylamine peptidase may also be used as disclosed in U.S. Pat. No. 4,767,702 which is hereby incorporated by reference for detecting specific species of the genus Neisseria. Further test reagents, may include, but are not limited to, hippuric acid for detecting Group B Streptococcus, L-pyrrolidonyl-beta-naphthylamide and esculin for detecting Group A Streptococcus, acid or mineral acid and sodium nitrite for extracting Group A Streptococcus antigen and tris-buffer, sodium chloride, EDTA, sodium azide and N-acetyl-cysteine for extracting Respiratory Syncytial Virus (RSV) antigen.

It will be understood by practitioners-in-the-art that multiple ampoules with guard arrangements may be disposed within the tubular housing of the collection device wherein each ampoule is separated by an absorbent plug. The number of frangible ampoules used is dependent on the need associated with the specimen collected and/or the particular test or immunoassay to be performed.

The collection devices described herein may be used for providing viable specimens for in vitro diagnostic testing methods, immunoassays for detecting and identifying microorganisms and for extracting detectable antigen. The collection devices may also be used in clinical situations to extract bacteria or other microorganisms from a clinical specimen for inoculation onto or into primary isolation media. The bacteria or microorganisms extracted by the collection devices may also be used for immunological or DNA/RNA probe testing or other tests to determine the identity and/or antimicrobial susceptibility pattern of the etiological agent.

EXAMPLE 1

RAPID CHROMOGENIC/COLORIMETRIC TEST TO IDENTIFY GROUP A STREPTOCOCCUS

A sampling site is contacted with a swab and a specimen, containing Group A Streptococcus is removed. The swab is inserted into a collection device having an ampoule associated with a guard arrangement.

The ampoule contains L-pyrrolidonyl-beta-naphthylamide. The ampoule is broken by way of the guard arrangement to release the L-pyrrolidonyl-betanaphthylamide. If the specimen develops no color, then the test is negative, however, if the specimen turns red, the specimen is positive for Group A Streptococcus.

EXAMPLE 2

RAPID CHROMOGENIC/COLORIMETRIC TEST TO IDENTIFY AND DIFFERENTIATE GROUP A STREPTOCOCCUS STRAINS FROM ENTEROCOCCI STRAINS

A sampling site is contacted with a swab and a specimen, containing Group A Streptococcus or Enterococci strains, is removed. The swab is inserted into a collection device having two ampoules and each ampoule associated with a guard arrangement.

The first ampoule contains L-pyrrolidonyl-beta-naphthylamide and the second ampoule contains esculin.

The first ampoule is broken by way of the guard arrangement to release the L-pyrrolidonyl-betanaphthaylamide. If the specimen develops no color, then the test is negative, however, if the specimen turns red, the specimen is positive for Group A Streptococcus.

The second ampoule is then broken by way of its guard arrangement to release the esculin. If no color develops then the specimen is positive for Group A Streptococcus, however, if a blue color develops then the specimen is positive for Enterococci.

EXAMPLE 3

EXTRACTION OF GROUP A STREPTOCOCCUS ANTIGEN FROM A THROAT SPECIMEN

A throat site is contacted with a swab and a specimen, possibly containing Group A Streptococcus, is removed. The swab is inserted into a collection device with a tubular housing and two ampoules disposed within. Each ampoule is associated with a guard arrangement.

The first ampoule contains an acid or mineral acid such as acetic acid, citric acid or hydrochloric acid and the second ampoule contains sodium nitrite.

The first and second ampoules are broken in succession to permit the formation of nitrous acid to cause the extraction of Group A Streptococcus antigen if present for further testing by an immunological based assay such as DIRECTIGEN® Rapid Group A Strep Test (trademark of Becton, Dickinson and Company, Franklin Lakes, N.J.) sold by Becton Dickinson Microbiology Systems, Cockeysville, Md.

EXAMPLE 4

RAPID PRESUMPTIVE CHROMOGENIC/COLORIMETRIC TEST FOR *NEISSERIA GONORRHOEAE* IN MALE URETHRAL DISCHARGE

A swab is inserted into a collection device with a tubular housing having two ampoules disposed within. Each ampoule is disposed within a guard arrangement.

The first ampoule contains a saline wetting agent and the second ampoule contains the reagent N,N,N,N-tetra-methyl-p-phenylenediamine dihydrochloride.

The first ampoule is broken to release the wetting agent onto the swab. The swab is then removed from the device to collect a male urethral discharge specimen. The swab is reinserted into the collection device with the collected specimen.

The second ampoule is then broken to release the reagent. If *N. gonorrhoeae* is present in the specimen, the reagent will turn purple or blue/purple.

What is claimed is:

1. An apparatus for collecting and transporting biological specimens comprising:
    an elongated tube having an open end and an opposite closed end;
    a specimen collector disposed within said tube comprising a cap, a shaft connected to said cap and a swab connected to said shaft;
    a guard arrangement disposed within said tube and located adjacent said closed end of said tube, comprising two rigid, movable and opposing members wherein each member comprises a forward end, a rearward end, and at least one sidewall comprising an inner surface, outer surface and an edge; a gap between said opposing edges of said members; and a cavity between said opposing inner surfaces of said members; and
    an ampoule associated with said cavity of said guard arrangement such that when said members of said guard arrangement are compressed said ampoule is ruptured.

2. The device of claim 1 wherein said gap is less than the thickness of said members.

3. The apparatus of claim 2 wherein said ampoule contains a culture-sustaining medium.

4. The apparatus of claim 3 wherein said ampoule comprises a frangible material.

5. The apparatus of claim 4 further comprising a plug of absorbent material located in said tube and positioned between said swab and said ampoule.

6. The apparatus of claim 1 wherein said tube and said cap are slidable relative to each other and form a slidable seal.

7. The apparatus of claim 1 wherein said shaft comprises a first and second end, wherein said first end is connected to said cap and said swab is connected to said second end.

8. The apparatus of claim 7 further comprising at least a second ampoule positioned within said tubular member and adjacent said plug.

9. The apparatus of claim 8 further comprising a second guard arrangement surrounding said second ampoule.

10. The apparatus of claim 9 wherein said second ampoule contains a test reagent.

11. The apparatus of claim 1 further comprising a plurality of ampoules disposed within said tube.

12. The apparatus of claim 11 further comprising a plurality of guard arrangements surrounding said plurality of ampoules.

13. A method for collecting and transporting biological samples with an apparatus having a tubular housing, a specimen collector disposed within said housing comprising a cap, a shaft connected to said cap and a swab connected to said shaft; a first guard arrangement comprising two rigid, movable and opposing members wherein each member comprises a forward end, a rearward end and at least one sidewall comprising an inner surface, an outer surface and an edge; a gap between said opposing edges of said members; a cavity between said inner surfaces of said members; and a first ampoule associated with said cavity, comprising:
    (a) contacting a sampling site with said swab;
    (b) obtaining a specimen from said site with said swab;
    (c) inserting the swab with the specimen into said housing;
    (d) closing said housing with said cap to protect said swab and said specimen from the environment external of said housing;
    (e) reducing said cavity and substantially eliminating said gap of said first guard arrangement by applying force to said outer surfaces of said members, such that said edges are brought together and said cavity is reduced and said first ampoule is ruptured;
    (f) releasing medium into said housing; and
    (g) subjecting said specimen to said medium.

14. The method of claim 13 wherein said gap is less than the thickness of said members.

15. The method of claim 14 wherein said ampoule comprises a test reagent for detecting and identifying microorganisms.

16. The method of claim 15 further comprising a second guard arrangement and a second ampoule, positioned within said tubular member and adjacent said first guard arrangement.

* * * * *